United States Patent [19]

Rudershausen

[11] Patent Number: 4,678,859

[45] Date of Patent: Jul. 7, 1987

[54] SYNTHESIS OF FLUOROCHLOROMETHANES

[75] Inventor: Charles G. Rudershausen, Kennett Square, Pa.

[73] Assignee: E. I. Du Pont de Nemours and Company, Wilmington, Del.

[21] Appl. No.: 889,468

[22] Filed: Jul. 25, 1986

[51] Int. Cl.$^4$ .............................................. C07C 17/24
[52] U.S. Cl. ................................................... 570/163
[58] Field of Search .......................................... 570/163

[56] References Cited

U.S. PATENT DOCUMENTS 3,087,975  4/1963  Hauptschein et al. .............. 260/653
3,087,976  4/1963  Hauptschein et al. .............. 260/653
3,322,692  5/1967  Clark ................................... 570/169

FOREIGN PATENT DOCUMENTS 1422476  11/1965  France .
134609  12/1974  Japan ................................... 570/169

Primary Examiner—J. E. Evans
Assistant Examiner—Joseph A. Boska
Attorney, Agent, or Firm—James E. Shipley

[57]  ABSTRACT

A vapor phase process for selective conversion of fluorodichloromethane and carbon tetrachloride to fluorotrichloromethane, difluordichlorlmethane, difluorochloromethane and chloroform by contacting a solid catalyst of an activated mixture of iron oxide and rare earth oxides.

5 Claims, No Drawings

SYNTHESIS OF FLUOROCHLOROMETHANES

BACKGROUND OF THE INVENTION

This invention relates to a vapor phase process for selective conversion of fluorodichloromethane ($CHCl_2F$) and carbon tetrachloride ($CCl_4$) to fluorotrichloromethane ($CCl_3F$), difluorodichloromethane ($CCl_2F_2$) and difluorochloromethane ($CHClF_2$) and by-product chloroform ($CHCl_3$) using a solid catalyst of an activated mixture of iron oxide and rare earth oxides.

Generally, fluorinated alkanes are produced commercially by liquid phase reaction of anhydrous hydrogen fluoride (HF) with chloroalkanes in the presence of a catalyst at superatmospheric pressure: Daudt et al., U.S. Pat. Nos. 2,005,705 and 2,005,708. This reaction is illustrated by the following equation using carbon tetrachloride as the representative haloalkane:

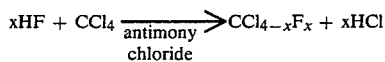

wherein x is 1 to 3. A mixture of products is obtained; the amount of each product depends on process conditions and feed ratios. In the above illustration, the overfluorinated product, trifluorochloromethane ($CClF_3$), is an undesired by-product whose vapor pressure is too high for significant commercial use and whose fluorine values are, therefore, usually wasted. Furthermore, the conventional process employs anhydrous HF, a particularly corrosive chemical which is very hazardous to handle. Hydrochloric acid (HCl) is a by-product and must be disposed of, either by considerable purification to eliminate residual halocarbons prior to sale, or by neutralization and disposal at significant expense and environmental risk. Finally, the antimony-based catalyst eventually loses both activity and selectivity, and must be disposed of with extreme caution because of environmental concerns relating particularly to possible contamination of surface and subsurface water.

French Patent No. 1,422,476 describes a catalyst for hydrofluorination of chlorocarbons to a range of fluorinated products. For example, anhydrous hydrofluoric acid is reacted with carbon tetrachloride in the vapor phase over an activated catalyst of iron and cerium oxides to form $CCl_3F$, $CCl_2F_2$ and $CClF_3$ and hydrochloric acid.

In U.S. Pat. No. 3,087,975, an activated alumina catalyst is disclosed for converting $CCl_2F_2$ primarily to $CClF_3$ and $CCl_4$. Similarly, in U.S. Pat. No. 3,087,976, monohydrofluorochloromethanes with one or two fluorine atoms are converted primarily to trifluoromethane ($CHF_3$) and $CHCl_3$ over activated alumina.

It is the object of the present invention to selectively synthesize the fluorochloromethanes of primary commercial interest without loss to overfluorinated products of little or no commercial utility. More specifically, the object of the present invention is a process effective under mild conditions without hydrogen fluoride feed or hydrochloric acid by-product formation, and without a catalyst whose eventual disposal poses serious environmental concerns.

SUMMARY OF THE INVENTION

In accordance with the present invention, a process has been discovered by which fluorochloromethanes are selectively and efficiently manufactured without hydrofluoric acid feed or hydrochloric acid by-product formation and at modest reaction conditions comprising reacting, in the vapor phase, fluorodichloromethane and carbon tetrachloride in the presence of an effective amount of a catalyst comprising a mixture of activated iron oxide and rare earth oxides at a sufficient temperature and pressure and for an adequate time to produce a reaction product containing fluorotrichloromethane, difluorodichloromethane, difluorochloromethane and chloroform. Thereafter, the fluorotrichloromethane, difluorodichloromethane, difluorochloromethane and chloroform can be separated from the reaction product and each product isolated, if desired. The reaction may be represented with the following equation:

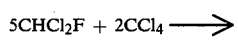

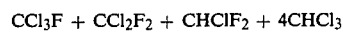

DETAILED DESCRIPTION OF THE INVENTION

The catalyst of this invention can contain different amounts of iron oxide and the oxides of various rare earth (RE) metals, such as scandium, yttrium, lanthanum, cerium, praseodymium, neodymium, illinium, samarium, europium, gadolinium, terbium, dysprosium, holmium, erbium, thulium, ytterbium and lutecium. The catalyst can also contain oxides of one or more of various other metals, including metals such as cobalt, zirconium, manganese, thorium and aluminum. However, the catalyst must contain some iron oxide and one or more oxides of various rare earths. Naturally occurring mixtures of rare earth oxides can be used as well as commercial preparations of these rare earth oxides.

One particularly preferred embodiment of the invention involves preparation of a coprecipitated catalyst by simultaneously combining aqueous solutions of iron nitrate ($Fe(NO_3)_3 \cdot 9H_2O$), a mixture of lanthanum-RE nitrates ($La-RE(NO_3)_3 \cdot 6H_2O$) and ammonium hydroxide ($NH_4OH$). The mixture of lanthanum-RE nitrates can be a mixture which is sold by Molycorp (subsidiary of Union Oil Co.) and designated in Molycorp's catalog of lanthanum-RE nitrate solutions as No. 5247. The specification and typical composition of No. 5247 is listed by Molycorp as follows:

| No. 5247* | Specification (wt.) |
|---|---|
| Total Rare Earth Oxides (REO's)** | 39.0% min. |
| $CeO_2$/REO | 1.0% max. |
| $Na_2O$ | 0.2% max. |
| CaO + SrO | — |
| Cl | 0.1% max. |
| Water Insolubles | 0.1% max. |
| pH of Solution | 1.5 max. |
| | Typical (wt.) |
| $Fe_2O_3$ | 0.02% |
| Heavy Metals (Pb + V + Ni + Cu) | 0.01% |
| MgO | 0.5% |

*As Solution: Concentration of La—$RE(NO_3)_3 \cdot 6H_2O$ solids in solution 55–65%.
**Typical Composition of the contained Rare Earth Oxides:

| Oxide | wt. | |
|---|---|---|
| Lanthanum ($La_2O_3$) | 66.0% | |
| Neodymium ($Nd_2O_3$) | 24.0% | |
| Cerium ($CeO_2$) | 0.7% | (1% max.) |
| Praseodymium ($Pr_6O_{11}$) | 8.2% | |
| Other REO | 1.1% | |
| Total | 100.0% | |

The precipitate which is formed is water-washed, dried and calcined to yield a catalyst containing iron oxide and rare earth oxides (REO's). After calcination, the catalyst can be crushed and screened to obtain a preferred particle size, such as 10 to 20 mesh.

Other methods can be used to prepare the catalyst of this invention and are well known to those skilled in the art of catalyst manufacture and include but are not limited to techniques such as physically mixing iron oxide and rare earth oxides together and thereafter pelletizing this mixture and using the pellets as formed or crushed to a desired particle size. Another method of preparation is to extrude a suitable slurry containing the desired iron nitrates and rare earth nitrates and thereafter to calcine and, if desired, crush to reduce particle size. Also, an inert surface or support such as granular alumina or activated carbon can be impregnated with an aqueous solution of iron and rare earth nitrates and thereafter the surface can be dried and calcined to remove the nitrates so as to leave iron oxide and rare earth oxides on the surface.

After preparation, the catalyst must be activated before use. This activation can be accomplished by any technique which contacts the catalyst with a vaporized fluorine-containing compound. One preferred method of activating the catalyst involves treating it in a reactor, which is subsequently to be used for the conversion reaction of this invention, with a vapor stream of either a fluorine-containing halocarbon or a mixture of HF and nitrogen. During this treatment, the temperature of the catalyst should be gradually increased to about 300 degrees Celsius and preferably up to about 450 degrees Celsius for a period of at least one hour.

After this activation, the catalyst is cooled and can be left in the reactor equipped with means by which $CHCl_2F$ and $CCl_4$ can be introduced into the reactor as vapors to contact an effective amount of the activated catalyst of this invention at effective process conditions to form fluorotrichloromethane, difluorodichloromethane, difluorochloromethane and chloroform. By effective amount of activated catalyst and effective process conditions is meant an amount of activated catalyst and process conditions which cause fluorotrichloromethane, difluorodichloromethane, difluorochloromethane and chloroform to be formed as the primary products of the reaction.

The operable ranges of process conditions include temperatures of about 50 to 300 degrees Celsius and catalyst contact times of about 0.1 to 30 seconds based on the volume of feed and the catalyst bed. The pressure may be subatmospheric, atmospheric or superatmospheric. The particular pressure used may be selected giving due consideration to the technique to be used for separating and isolating the reaction products. The reaction is preferably operated at 0.1 to 30 atmospheres pressure and the preferred temperature range is about 75 to 200 degrees Celsius, and the preferred catalyst contact times are about 0.1 to 5 seconds. The particularly preferred process conditions are a temperature of 200 degrees Celsius, atmospheric pressure, a catalyst contact time of 3 seconds and an equimolar feed ratio of the reactants.

The process of this invention may use any appropriate reactor. A shell and tube reactor is particularly desirable in which the catalyst is contained in the tubes from which the heat of reaction is transferred to water on the shell side. If the reaction temperature is over 100 degrees Celsius, steam can be produced and the pressure selected to correspond to the reaction temperature desired in the catalyst bed.

Continuous or batch distillation can be used to separate the reaction products and unreacted $CHCl_2F$, which can be recycled. By-product chloroform can be recovered and utilized in a separate process to produce further $CHCl_2F$, if desired.

The following examples illustrate particular aspects of the present invention:

EXAMPLE 1

A catalyst was prepared, first by making the following separate solutions:

(a) 244 g of $Fe(NO_3)_3.9H_2O$ in 400 g of distilled water
(b) 100 g of 60% solution of rare earth nitrates (La-RE$(NO_3)_3.6H_2O$) manufactured by Molycorp (subsidiary of Union Oil Co.) and designated in the manufacturer's catalog of rare earth nitrate solutions as No. 5247. The typical composition is listed by Molycorp as follows:

| No. 5247* | Specification (wt.) |
|---|---|
| Total Rare Earth Oxides (REO's)** | 39.0% min. |
| $CeO_2$/REO | 1.0% max. |
| $Na_2O$ | 0.2% max. |
| CaO + SrO | — |
| Cl | 0.1% max. |
| Water Insolubles | 0.1% max. |
| pH of Solution | 1.5 max. |
| | Typical (wt.) |
| $Fe_2O_3$ | 0.02% |
| Heavy Metals (Pb + V + Ni + Cu) | 0.01% |
| MgO | 0.5% |

*As Solution: Concentration of La—RE$(NO_3)_3.6H_2O$ solids in solution 55–65%.
**Typical Composition of the contained Rare Earth Oxides:

| Oxide | wt. | |
|---|---|---|
| Lanthanum ($La_2O_3$) | 66.0% | |
| Neodymium ($Nd_2O_3$) | 24.0% | |
| Cerium ($CeO_2$) | 0.7% | (1% max.) |
| Praseodymium ($Pr_6O_{11}$) | 8.2% | |
| Other REO | 1.1% | |
| Total | 100.0% | |

(c) 160 ml of 28% aqueous $NH_4OH$ in 800 ml of distilled water

The nitrate solutions were combined in a single separatory funnel; the ammonium hydroxide solution was charged to another separatory funnel. Each of these two funnels was equipped with rubber tubing extensions to the bottom of a 2-liter beaker outfitted with a magnetic stirring bar and a pH meter probe just over the stirring bar. Both the nitrate and the ammonium hydroxide solutions were separately preheated to 80 degrees Celsius and the discharged simultaneously over a period of about fifteen minutes at rates adjusted to keep the pH in the mixing zone between 8.5 and 9.5. Stirring was continued for 1 hour while the contents of the beaker were cooled to 65 degrees Celsius, after which the pH was adjusted back to 8.5 with incremental addition of ammonium hydroxide solution. The precipitate was vacuum-filtered, displacement-washed with 2 liters of distilled water, heated to 65 degrees Celsius, vacuum-dried at 170 degrees Celsius and finally calcined for 6 hours at 500 degrees Celsius. 70 g of hard particles were obtained which were thereafter crushed and screened for the 10 to 20 mesh particle size range used as described further herein. The catalyst contained oxides at approximately a 63:37 weight ratio of iron:rare earth metals.

Five cubic centimeters of the catalyst were charged to a 7 cc Inconel reactor tube placed in a sand bath with temperature-controlled electric heaters. The catalyst was activated by first raising its temperature to 150 degrees Celsius by passing heated nitrogen over the catalyst for a two hour period at 100 std. cu. cm./min. (sccm). Thereafter, vaporized anhydrous HF was further added at 30 sccm while continuing nitrogen addition at the original rate during further heating to 300 degrees Celsius over a 1 hour period. Nitrogen and HF were then reduced to 25 sccm each while slowly cooling to 100 degree Celsius.

EXAMPLE 2

The activated catalyst (5 cc) of Example 1 was left in the reactor which was placed in a thermally controlled sand bath and equipped with feed parts whereby $CHCl_2F$ and $CCl_4$ were continuously fed as vapors through a mass flow meter at 42 and 14 sccm, respectively, at essentially 1 atmosphere pressure. Contact time was a nominal 3 seconds in the catalyst bed based on the volume of the catalyst bed and the volumetric rate of the $CHCl_2F$ vapor feed (taken at 250 degrees Celsius and 1 atm.). Product effluent was measured with a flame ionization gas chromatograph. As shown in the table for this example, selectivity was excellent, with only 0.3% $CHF_3$ and no $CClF_3$ in the effluent. At a nominal contact time of 3 seconds, conversion of $CCl_4$ was 88%, showing high catalyst activity as well.

EXAMPLES 3-5

Using the catalyst of Example 1 and the procedures of Example 2 modified to illustrate amenability to various temperatures (100 to 200 degrees Celsius) and retention times (1 to 3 seconds, as defined in Example 2), good activity and selectivity are shown in the Table. At 200 degrees Celsius, equimolar $CCl_4$ and $CHCl_2F$ feed and a contact time of 3 seconds, no overfluorinated products ($CHF_3$ and $CClF_3$) were detected in the effluent (Example 5).

The description and examples are not intended to limit the scope of the invention, especially with respect to specific composition and proportions of the iron and rare earths used or the mode of catalyst preparation.

TABLE

| | EXAMPLE | | | |
|---|---|---|---|---|
| | 2 | 3 | 4 | 5 |
| T (°C.) | 200 | 100 | 200 | 200 |
| Mole Feed Ratio $CHCl_2F/CCl_4$ | 3/1 | 3/1 | 3/1 | 1/1 |
| CT* (sec) | 3 | 3 | 1 | 3 |
| Effluent Composition | Mole % | | | |
| $CCl_4$ | 2.9 | 2.2 | 2.0 | 8.1 |
| $CCl_2F$ | 13.2 | 15.8 | 15.5 | 36.6 |
| $CCl_2F_2$ | 8.6 | 4.4 | 6.0 | 5.8 |
| $CClF_3$ | 0.0 | 0.0 | 0.0 | 0.0 |
| $CHCl_3$ | 49.1 | 43.0 | 43.5 | 39.6 |
| $CHCl_2F$ | 15.4 | 23.0 | 24.0 | 8.3 |
| $CHClF_2$ | 10.5 | 11.2 | 8.8 | 1.5 |
| $CHF_3$ | 0.3 | 0.4 | 0.2 | 0.0 |

*Catalyst contact time based on 250° C., 5 cc catalyst and 1 atm.

I claim:

1. A process comprising contacting, in the vapor phase, fluorodichloromethane and carbon tetrachloride with an effective amount of a catalyst comprising an activated mixture of iron oxide and rare earth metal oxides at a sufficient temperature and pressure and for an adequate time to produce a reaction product containing fluorotrichloromethane, difluorodichloromethane, difluorochloromethane and chloroform.

2. The process of claim 1 wherein the temperature is about 50 to 300 degrees Celsius, the pressure is about 0.1 to 30 atmospheres, and the contact time of the fluorodichloromethane and carbon tetrachloride vapors with the activated catalyst is about 0.1 to 30 seconds.

3. The process of claim 1 wherein the catalyst consists essentially of an activated mixture of iron oxide and rare earth oxides.

4. The process of claim 1 wherein the catalyst of an activated mixture of iron oxide and rare earth oxides includes at least one member selected from the group consisting of oxides of cobalt, zirconium, manganese, thorium, and aluminum.

5. The process of claim 1 wherein the catalyst is used on a support.

* * * * *